United States Patent [19]

Chiarino et al.

[11] Patent Number: 4,863,908

[45] Date of Patent: * Sep. 5, 1989

[54] MONO(2-AMMONIUM-2-HYDROXYMETHYL-1,3 PROPANEDIOL)(2R-CIS)-3-METHYLOXIRANYL)PHOSPHONATE, ITS PREPARATION AND PHARMACEUTICAL COMPOSITIONS CONTAINING IT

[75] Inventors: Dario Chiarino, Monza; Davide Della Bella; Vittorio Ferrari, both of Milan, all of Italy

[73] Assignee: Zambon S.p.A., Milan, Italy

[*] Notice: The portion of the term of this patent subsequent to Feb. 23, 2005 has been disclaimed.

[21] Appl. No.: 97,425

[22] Filed: Sep. 15, 1987

Related U.S. Application Data

[63] Continuation of Ser. No. 819,005, Jan. 14, 1986, abandoned, which is a continuation of Ser. No. 355,372, Mar. 8, 1982, abandoned, which is a continuation of Ser. No. 196,033, Oct. 10, 1980, abandoned.

[30] Foreign Application Priority Data

Oct. 18, 1979 [IT] Italy ............................... 26581 A/79

[51] Int. Cl.$^4$ ............................................. A01N 43/04
[52] U.S. Cl. ....................................... 514/76; 547/217
[58] Field of Search ........................................... 514/76

[56] References Cited

U.S. PATENT DOCUMENTS

| | | | |
|---|---|---|---|
| 3,322,767 | 5/1967 | Nahas | 260/343.7 |
| 3,641,063 | 2/1972 | Miller | 260/348.42 |
| 3,914,231 | 10/1975 | Hendlin et al. | 260/348.42 |
| 3,940,483 | 2/1976 | Dursch | 424/246 |

FOREIGN PATENT DOCUMENTS

| | | |
|---|---|---|
| 2205272 | 8/1872 | Fed. Rep. of Germany . |
| 2134672 | 1/1973 | Fed. Rep. of Germany . |
| 2158828 | 11/1985 | United Kingdom . |

OTHER PUBLICATIONS

Chemical Abstracts, vol. 81, 96448y.
Chemical Abstracts, vol. 82, 119344y.
Hendlin et al, Science, vol. 66 (1969), pp. 122–123.
The U.S. Pharmacopeia 21st Revision, 1984, Title page, Copyright page, and p. 7.
Handbook of Nonprescription Drugs, Seventh Ed., 1982, Title page, Copyright page, and pp. 27 and 81.
Antimicrobial Agents and Chemotherapy, 1969, pp. 322–326.
Boll. Del. Soc. Italiana de Farmacie Ospedaliera, XXIV, 1978, Title page, Copyright page, and pp. 285–292.
Journal of Chromatography, 224, 1981, pp. 257–264.
Acta Path. et Microbiol., Section B, 1971, Supplement No. 217, Title page and pp. 6–8 and 67–71.
Journal of Antimicrobial Chemotherapy, 1983, 12, pp. 357–361.
Eur. Urol, 13, Supp 1, pp. 42–44 (1987), and pp. 80–85 (1987).
The Extra Pharmocopoeia, 1982, Cover page, and p. 1165.
Drugs of the Future, vol. 11, No. 1, 1986, pp. 16–17.
Future Trends in Chemotherapy, 1974, pp. 161–168.
A Copy of the Jan. 1987 issue of "European Urology".

*Primary Examiner*—Catherine L. Mills
*Attorney, Agent, or Firm*—Stevens, Davis, Miller & Mosher

[57] ABSTRACT

Mono(2-ammonium-2-hydroxymethyl-1,3-propanediol)(2R-cis)-(3-methyloxiranyl) phosphonate endowed with therapeutic activity as broad-spectrum antibiotic, as well as a method for preparing same from bis(2-ammonium-2-hydroxymethyl-1,3-propanediol)(2R-cis)-(3-methyloxiranyl) phosphonate and a sulphonic acid. Pharmaceutical compositions containing the novel mono(2-ammonium-2-hydroxymethyl-1,3-propanediol)(2R-cis)-(3-methyloxiranyl) phosphonate are disclosed.

2 Claims, No Drawings

MONO(2-AMMONIUM-2-HYDROXYMETHYL-1,3 PROPANEDIOL)(2R-CIS)-3-METHYLOXIRANYL)-PHOSPHONATE, ITS PREPARATION AND PHARMACEUTICAL COMPOSITIONS CONTAINING IT

This application is a continuation of application Ser. No. 819,005, filed Jan. 14, 1986, which is in turn a continuation of application Ser. No. 355,372, filed Mar. 8, 1982, which is in turn a continuation of application Ser. No. 196,033, filed on Oct. 10, 1980, all abandoned.

The present invention relates to a new soluble salt of (2R-cis)-(3-methyloxiranyl)phosphonic acid, the preparation thereof as well as the pharmaceutical compositions containing it.

The new salt of the invention, is the mono(2-ammonium-2-hydroxymethyl-1,3-propanedio)(2R-cis)-(3-methyloxiranyl)phosphonate of the formula:

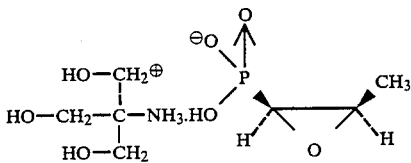

(2R-cis)-(3-methyloxiranyl)phosphonic acid is also known as fosfomycin (Merck Index—9th Edition—4110).

Fosfomycin and the salts thereof with non-toxic bases are widely used in human and veterinary fields to inhibit the grouth of gram-positive and gram-negative pathogenous bacteria. In the Italian patent application No. 25,853 A/78 filed on July 19, 1978 corresponding to U.S. patent application Ser. No. 256,396 (filed on Apr. 22, 1981), abandoned a continuation of U.S. patent application Ser. No. 57,801 (filed on July 16, 1979) now abandoned, there was disclosed and claimed the bis(2-ammonium-2-hydroxymethyl-1,3-propanediol)(2R-cis)-(3-methyloxiranyl)phosphonate showing a tolerability and bioavailability remarkably more favourable than those of the sodium and calcium salts of fosfomycin.

However bis(2-ammonium-2-hydroxymethyl-1,3-propanediol)(2R-cis)-(3-methyloxiranyl)phosphonate gives very viscous solutions thus rendering difficult the administration of the salt by injectable route.

The Applicant has now found that mono(2-ammonium-2-hydroxymethyl-1,3-propanediol)(2R-cis)-(3-methyloxiranyl)phosphanate of the invention, while maintaining the advantages of bis(2-ammonium-2-hydroxymethyl-1,3-propanediol)(2R-cis)-(3-methyloxiranyl)phosphonate unchanged, has the further advantage to give solutions less viscous than those which can be obtained, the content of conventional fosfomycin being equal, when using bis(2-ammonium-2-hydroxymethyl-1,3-propanediol)(2R-cis)-(3-methyloxiranyl)-phosphonate.

More particularly, a solution consisting of 688 mg and 1377 mg respectively of bis(2-ammonium-2-hydroxymethyl-1,3-propanediol)(2R-cis)-(3-methyloxiranym)-phosphate (corresponding to 250 mg and 500 mg respectively of conventional fosfomycin) in 2.5 ml of water solvent, shows a viscosity of 4.8 and 7.2 cps respectively, at 25° C. The corresponding solutions obtained by dissolving 470 mg and 940 mg respectively of mono(2-ammonium-2-hydroxymethyl-1,3-propanediol)(2R-cis)-(3-methyloxiranyl)phosphonate in 2.5 ml of wter solvent show at 25° C. a viscosity of 3.9 and 5.0 cps respectively.

Typical pharmaceutical preparations are:
(a) Administration by oral route (sachets)

The compositions for the oral route administration corresponding to 250 mg, 500 mg and 2000 mg of conventional fosfomycin contain (the amounts are in milligrams):

| | | | |
|---|---|---|---|
| Mono(2-ammonium-2-hydroxymethyl-1,3-propanediol)(2R-cis)-(3-methyloxiranyl)phosphonate | 470 | 940 | 3760 |
| sodium carboxymethycellulose | 80 | 100 | 120 |
| lactose | 50 | 100 | 300 |
| titanium dioxide | 50 | 70 | 100 |
| orange flavour | 50 | 50 | 80 |
| saccharose | 2300 | 2740 | 5640 |

(b) Administration by parenteral route

For the administration by parenteral route a vial and an ampoule of water for injectable preparation is used as solvent.

Each vial contains 470, 940 or 1880 mg respectively of the salt of the invention, in form of sterile powder.

At the time of administration, the sterile powder is dissolved in the solvent.

The amounts of solvent are 2.5 ml for each vial containing 470 mg and 940 mg of the salt of the invention and 5.0 ml for each vial containing 1880 mg of the compound of the invention.

The mono(2-ammonium-2-hydroxymethyl-1,3-propanediol)(2R-cis)-(3-methyloxiranyl)phosphonate of the present invention is prepared by reacting the bis(2-ammonium-2-hydroxymethyl-1,3-propanediol)(2R-cis)-(3-methyloxiranyl)phosphonate, prepared according to Italian patent application No. 25,853 A/78, corresponding to U.S. patent application Ser. No. 256,396 (filed on Apr. 22, 1981), abandoned a continatuion of U.S. patent application Ser. No. 57,801 (filed on July 16, 1979) now abandoned, with a sulphonic acid, such as for instance an alkylsulphonic, aralkylsulphonic, arylsulphonic acid.

The preparation of the salt of the invention and the physico-chemical characteristics of the obtained product, are illustrated in the following example, which is however in any way limitative.

EXAMPLE

A solution, previously heated at 75° C., of 262.5 g (1.38 mol) of monohydrated 4-toluensulphonic acid in 1300 ml of absolute ethyl alcohol was added to a suspension of 500 mg (1.315 mol) of bis(2-ammonium-2-hydroxymethyl-1,3-propanediol)(2R-cis)-(3-methyloxiranyl)phosphonate in 3300 ml of absolute ethyl alcohol, heated under stirring at 70°–75° C.

At first the reagents go almost completely on solution and thereafter a colorless crystalline solid begins to slowly precipitate. The suspension is slowly cooled under stirring to +3° C., by means of a water-ice bath.

The precipitate is then collected by filtration under vacuum and washing on the filter with 700 ml of absolute ethyl alcohol cooled to +10° C.

After drying under vacuum at 40° C. for 16 hours, 291.3 g of the acid salt are obtained in form of a colorless microcrystalline powder which melts at 116° C.

The product can be purified to be analysed by disolution in warm in methanol (ratio 1:2 p/v) and treatment of the thus obtained solution, under agitation and cooling to +3° C., with 4 volume of absolute ethyl alcohol.

$^1$H-NMR (D$_2$O): (ppm=1.53 (d, 3H, CH$_3$), 3.50–2.75 (m, 2H, CH), 3.75 (s, 6H, CH$_2$).

$[\alpha]_{365}^{20}$ (5% water) −12.5° C.

IR (in KBr): 800 e 900 cm$^{-1}$.

We claim:

1. A method for treating infections due to gram-positive and gram-negative pathogenic bacteria comprising subjecting by oral administration such bacteria to a composition containing an effective growth-inhibiting amount of a salt which is a substantially pure mono (2-ammonium-2-hydroxymethyl-1,3-propanediol) (2R-cis)-(3-methyloxiranyl)phosphonate.

2. A method as defined in claim 1, in which the salt is present in the composition in association with a pharmaceutically-acceptable inert carrier.

* * * * *

UNITED STATES PATENT AND TRADEMARK OFFICE

CERTIFICATE EXTENDING PATENT TERM
UNDER 35 U.S.C. § 156

PATENT NO.     :   4,863,908

ISSUED         :   September 5, 1989

INVENTOR(S)    :   Dario Chiarino et al.

PATENT OWNER   :   Zambon Group, S.p.A.

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of 1,527 days from February 23, 2005, the original expiration date of the patent, subject to the provisions of 35 U.S.C. § 41(b), with all rights pertaining thereto as provided by 35 U.S.C. § 156(b).

I have caused the seal of the Patent and Trademark Office to be affixed this 27th day of August 1998.

Bruce A. Lehman
Assistant Secretary of Commerce and
Commissioner of Patents and Trademarks